(12) United States Patent
Yao

(10) Patent No.: US 11,452,359 B2
(45) Date of Patent: Sep. 27, 2022

(54) TOUCHING HEAD FOR COSMETIC DEVICE AND COSMETIC DEVICE USING THE SAME

(71) Applicant: Guanyin Yao, Guangdong Province (CN)

(72) Inventor: Guanyin Yao, Guangdong Province (CN)

(*) Notice: Subject to any disclaimer, the term of this patent is extended or adjusted under 35 U.S.C. 154(b) by 123 days.

(21) Appl. No.: 17/027,736

(22) Filed: Sep. 22, 2020

(65) Prior Publication Data
US 2022/0087401 A1 Mar. 24, 2022

(51) Int. Cl.
| A45D 44/00 | (2006.01) |
| A61K 8/25 | (2006.01) |
| A61N 5/06 | (2006.01) |
| A61Q 19/00 | (2006.01) |
| F21V 19/00 | (2006.01) |
| F21V 29/87 | (2015.01) |
| F21Y 115/10 | (2016.01) |

(52) U.S. Cl.
CPC ................ *A45D 44/00* (2013.01); *A61K 8/25* (2013.01); *A61N 5/0616* (2013.01); *A61Q 19/00* (2013.01); *F21V 19/003* (2013.01); *F21V 19/005* (2013.01); *F21V 29/87* (2015.01); *A45D 2200/1009* (2013.01); *A45D 2200/155* (2013.01); *A61N 2005/0644* (2013.01); *A61N 2005/0652* (2013.01); *F21Y 2115/10* (2016.08)

(58) Field of Classification Search
CPC .... A61B 18/20–18/28; A61N 5/06–2005/073; A61N 2005/0644

USPC ..................... 606/2–19; 607/88–94
See application file for complete search history.

(56) References Cited

U.S. PATENT DOCUMENTS

| 9,339,665 B2 | 5/2016 | Tsao | |
| 2007/0038206 A1* | 2/2007 | Altshuler | A46B 15/0036 606/20 |
| 2009/0306607 A1 | 12/2009 | Yasuhiro | |
| 2011/0254450 A1* | 10/2011 | Bergholz | H05B 45/58 315/121 |
| 2012/0002426 A1* | 1/2012 | Wang | F21K 9/23 362/373 |
| 2012/0109266 A1 | 3/2012 | Waldman | |

FOREIGN PATENT DOCUMENTS

CN 209790628 U 12/2019

* cited by examiner

*Primary Examiner* — Jonathan T Kuo
*Assistant Examiner* — Vyann V Huh

(57) ABSTRACT

The present invention provides a touching head for cosmetic device and a cosmetic device using the same, the touching head includes a holder and a touch pad, the upper and lower openings of the holder are connected, wherein the holder is provided with a washer, and the top of the washer is fixedly connected with the touch pad. the touch pad of the touching head of the invention is made of toughened glass, which is only a simple sheet portion without additional processing, its surface is smooth, soft and transparent, which can provide good touch feeling when contacting with human skin, and has the advantages of simple structure, excellent waterproof performance and low production cost. In addition, the heat emitted by the LED light board of the cosmetic device can be effectively transmitted to the touching head, so that the therapeutic effect of the cosmetic device is better.

7 Claims, 4 Drawing Sheets

TOUCHING HEAD FOR COSMETIC DEVICE AND COSMETIC DEVICE USING THE SAME

FIELD OF THE INVENTION

The present invention relates to a field of cosmetic device, and more particularly relates to a touching head for cosmetic device and a cosmetic device using the same.

BACKGROUND OF THE INVENTION

Cosmetic device is a kind of device for improving human skin. Conventional touching head of a cosmetic device is usually made of metal materials such as stainless steel, which has a high cost, and the touch feeling of skin is not comfortable when contacting with it. Furthermore, metal touching head does not have light transmittance, which leads to a need of opening additional light holes on the surface of the touching head, and the uneven surface of the touching head further reduces the comfort of the cosmetic device, so the user experience is poor. Besides, metal touching head also leads to a small luminous area of LED treatment lights in the cosmetic device, which affects its normal use. In a patent document with a publication number of "CN201920221242", a household led wrinkle removing and acne removing cosmetic device head is disclosed. The treatment comfort of the cosmetic device is improved by using glass instead of metal material to make the touching head, however, the glass head of the cosmetic device is a special-shaped portion processed as a whole, and its vulnerability makes the production and processing of glass head difficult and high-cost.

SUMMARY OF THE INVENTION

In order to solve the problem of the prior arts, it is necessary to provide a touching head for cosmetic device with simple structure and low cost.

The present invention provides a touching head for cosmetic device, includes a holder and a touch pad, the upper and lower openings of the holder are connected, wherein the holder is provided with a washer, and the top of the washer is fixedly connected with the touch pad.

Preferably, the inner wall of the holder is provided with a bearing ring for placing the washer, the bearing ring is provided with a threaded through hole, and the bottom of the washer is provided with a connecting screw hole corresponding to the threaded through hole.

Preferably, touching head further includes a waterproof groove is arranged on the outer wall of the washer, and a waterproof ring is installed in the waterproof groove, the waterproof ring is clamped between the washer and the holder when the touching head is assembled.

Preferably, the top end of the washer is provided with a gluing step.

Preferably, the touch pad is made of toughened glass.

Preferably, the washer is made of metal material.

The present invention further provides a cosmetic device using the touching head, the cosmetic device further includes a shell and an LED light board fixed on the shell, the LED light board is welded with a spring, the surface of the LED light board is pasted with thermal conductive silica gel, the holder is installed on the shell and is located at the periphery of the LED light board when assembled.

Preferably, the thermal conductive silica gel is provided with through holes corresponding to light beads position on the LED light board.

The invention has the following beneficial effects: the touch pad of the touching head of the invention is made of toughened glass, which is only a simple sheet portion without additional processing, its surface is smooth, soft and transparent, which can provide good touch feeling when contacting with human skin, and has the advantages of simple structure, excellent waterproof performance and low production cost. In addition, the heat emitted by the LED light board of the cosmetic device can be effectively transmitted to the touching head, so that the therapeutic effect of the cosmetic device is better.

BRIEF DESCRIPTION OF THE DRAWINGS

The following drawings of the present invention are used to understand the invention as a part of it. The drawings show an embodiment and the description of the embodiment, so as to explain the principle of the invention, in which.

DETAILED DESCRIPTION OF THE EMBODIMENTS

Figure 1:
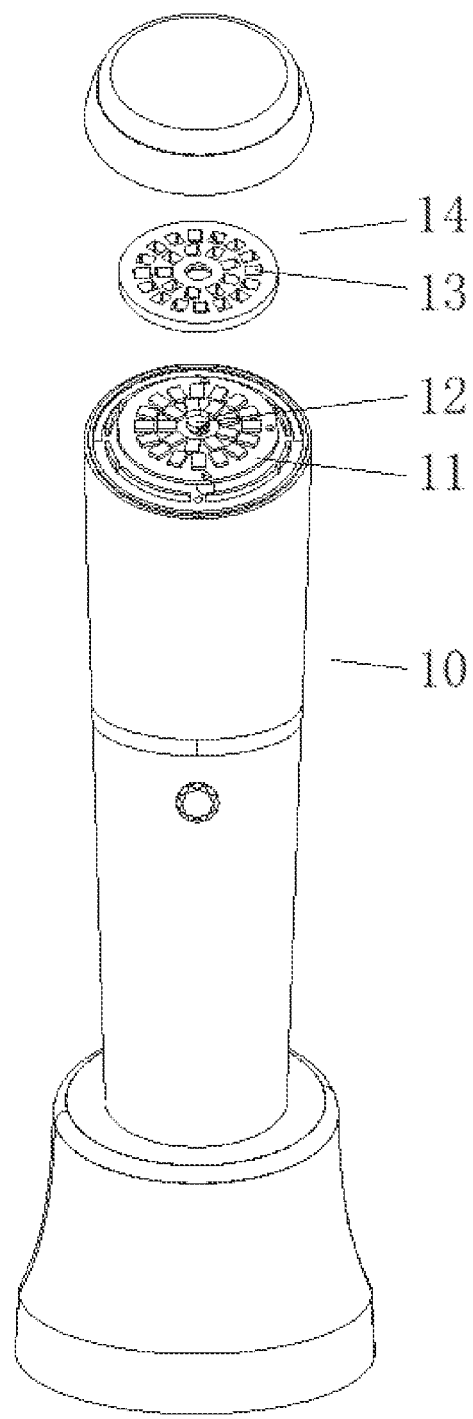
FIG. 1 shows the partial decomposition of the cosmetic device of the present invention.

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. In the drawings, the size and the relative dimension of layers and areas may be exaggerated for clear. Like numbers refer to like elements throughout.

It should be understood that if a component or a layer is described as "on", "adjacent to", "connected to" or "coupled to" another component or layer, it may be directly configured on, adjacent to, connected to or coupled to the other component, or there may be a mediate component or a mediate layer. Rather, if a component or a layer is described as "directly on", "directly adjacent to", "directly connected to" or "directly coupled to" another component or layer, mediate component or mediate layer does not exist.

Figure 2:
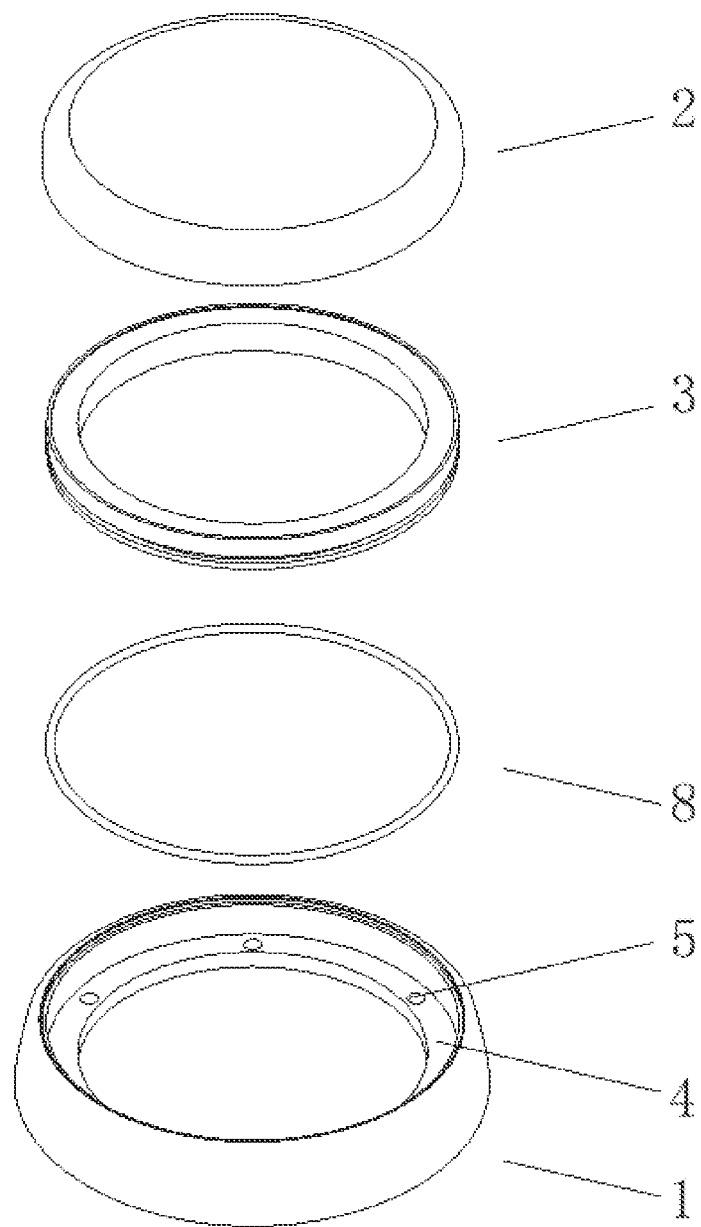
FIG. 2 shows the exploded view of the touching head of the present invention.
Figure 3:
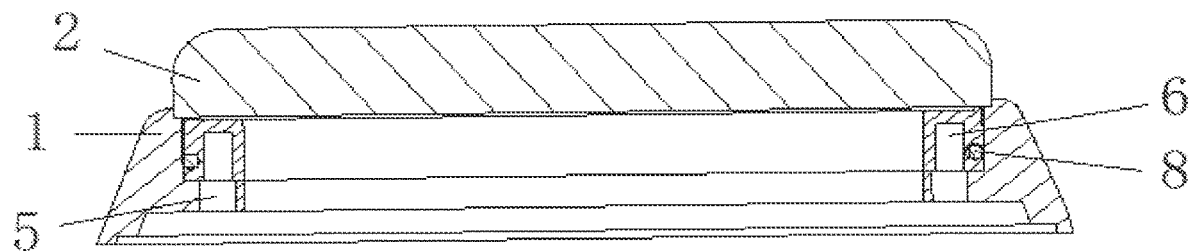
FIG. 3 shows the sectional view of the touching head of the present invention.
Figure 5:
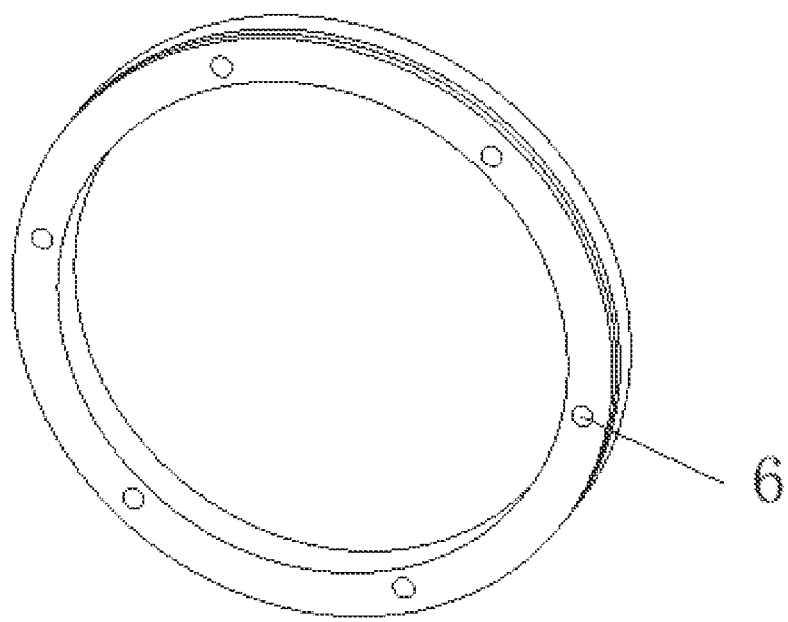
FIG. 5 shows the schematic diagram of the bottom structure of the washer of the present invention.

Referring to FIG. 2, FIG. 3 and FIG. 5, a touching head for cosmetic device includes a holder 1 and a touch pad 2, the upper and lower openings of the holder 1 are connected, the holder 1 is provided with a washer 3, and the top of the washer 3 is fixedly connected with the touch pad 2. The touch pad 2 is made of glass material, which is a simple sheet-like portion without additional processing. The surface of the touch pad 2 is smooth, soft and transparent, which can provide good touch feeling when contacting with human skin. The touch pad 2 can also be made of jade and other transparent and harmless materials. The washer 3 is made of metal material.

The inner wall of the holder 1 is provided with a bearing ring 4 for placing the washer 3. The bearing ring 4 is provided with a threaded through hole 5, and the bottom of the washer 3 is provided with a connecting screw hole 6 corresponding to the threaded through hole 5. In the present embodiment, the washer 3 is fixedly connected to the holder 1 by using a screw to pass through the threaded through hole 5 from bottom to top, and connect with the connecting screw hole 6 through the screw. The holder 1 and the washer 3 can also be provided with mutually matched clamps for clamping and connecting, so as to realize the connection and fixation of the two.

Figure 4:
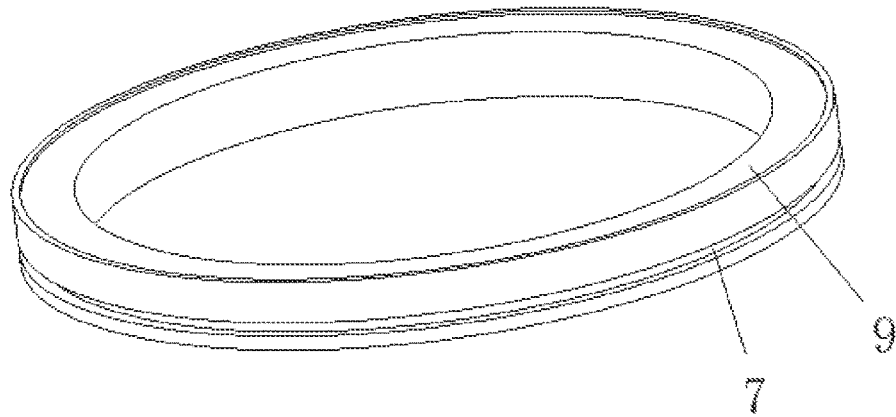
FIG. 4 shows the structural diagram of the washer of the present invention.

Referring to FIG. 4, a waterproof groove 7 is arranged on the outer wall of the washer 3, and a waterproof ring 8 is installed in the waterproof groove 7, the waterproof ring 8 is clamped between the washer 3 and the holder 1 when the touching head is assembled, which is able to provide good water resistance for the touching head.

The top end of the washer 3 is provided with a gluing step 9. The washer 3 is fixedly connected to the touch pad 2 by coating with thermal conductive adhesive on the gluing step 9, which is able to prevent the glue from spilling out of the touching head and keep the beauty of the touching head.

The touch pad 2 is made of toughened glass, therefore the firmness of the touch pad 2 is improved and the service life of the touching head is prolonged.

Referring to FIG. 1, a cosmetic device using the touching head further includes a shell 10 and an LED light board 11 fixed on the shell 10. The LED light board 11 is welded with a spring 12, the surface of the LED light board 11 is pasted with thermal conductive silica gel 13, and the holder 1 is installed on the shell 10 and is located at the periphery of the LED light board 11 when assembled. The top end of the spring 12 is against the bottom of the touch pad 2, and the thermal conductive silica gel 13 can effectively transfer the heat of the LED light board 11 to the touching head, so as to improve the therapeutic effect of the cosmetic device.

The thermal conductive silica gel 13 is provided with through holes corresponding to light beads position on the LED light board 11, and the thermal conductive silica gel 13 is not covered on the light beads of the LED light board 11, so as to avoid the influence of light attenuation on the LED light board 11, and improve the light output efficiency.

Although the present invention has been described with reference to the embodiments thereof and the best modes for carrying out the present invention, it is apparent to those skilled in the art that a variety of modifications and changes may be made without departing from the scope of the present invention, which is intended to be defined by the appended claims.

What is claimed is:

1. A touching head for cosmetic device, comprising a holder and a touch pad, upper and lower openings of the holder are connected, wherein the holder is provided with a washer, and the top of the washer is fixedly connected with the touch pad; the touch pad is configured to provide touch feeling when contacting with user's skin;

wherein an inner wall of the holder is provided with a bearing ring for bearing the washer;

an inner diameter of the bearing ring is smaller than an external diameter of the washer, such that the bearing ring is capable of bearing the washer;

a gluing step is arranged on a top end of the washer; the gluing step is configured to prevent a glue from spilling out of the touching head.

2. The touching head for cosmetic device according to claim 1, wherein the bearing ring is provided with a threaded through hole, and the bottom of the washer is provided with a connecting screw hole corresponding to the threaded through hole.

3. The touching head for cosmetic device according to claim 1, further comprises a waterproof groove arranged on an outer wall of the washer, and a waterproof ring installed in the waterproof groove, wherein the waterproof ring is clamped between the washer and the holder when the touching head is assembled.

4. The touching head for cosmetic device according to claim 1, wherein the touch pad is made of toughened glass.

5. The touching head for cosmetic device according to claim 1, wherein the washer is made of metal material.

6. A cosmetic device using the touching head according to claim 1, comprising a shell and an LED light board fixed on the shell, wherein the LED light board is welded with a spring, wherein a surface of the LED light board is pasted with thermal conductive silica gel, wherein the holder is installed on the shell and is located at a periphery of the LED light board when assembled.

7. The cosmetic device according to claim 6, wherein the thermal conductive silica gel is provided with through holes corresponding to light beads position on the LED light board.

\* \* \* \* \*